United States Patent
Chen et al.

(10) Patent No.: US 8,519,194 B2
(45) Date of Patent: *Aug. 27, 2013

(54) PROCESS FOR PRODUCING CYCLOHEXYLBENZENE

(75) Inventors: Tan-Jen Chen, Kingwood, TX (US); Francisco M. Benitez, Houston, TX (US); John S. Buchanan, Lambertville, NJ (US); Jane C. Cheng, Bridgewater, NJ (US); Jon E. Stanat, Westhampton Beach, NY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 29 days.

This patent is subject to a terminal disclaimer.

(21) Appl. No.: 13/145,007

(22) PCT Filed: Nov. 24, 2009

(86) PCT No.: PCT/US2009/065692
§ 371 (c)(1),
(2), (4) Date: Aug. 9, 2011

(87) PCT Pub. No.: WO2010/098798
PCT Pub. Date: Sep. 2, 2010

(65) Prior Publication Data
US 2011/0288341 A1    Nov. 24, 2011

Related U.S. Application Data

(60) Provisional application No. 61/155,733, filed on Feb. 26, 2009.

(51) Int. Cl.
*C07C 45/27* (2006.01)
*C07C 27/08* (2006.01)
*C07C 2/64* (2006.01)
*C07C 2/66* (2006.01)

(52) U.S. Cl.
USPC ............ 568/361; 568/708; 585/446; 585/467

(58) Field of Classification Search
USPC ......................... 568/361, 798; 585/446, 467
See application file for complete search history.

(56) References Cited

U.S. PATENT DOCUMENTS

| | | |
|---|---|---|
| 3,197,399 A | 7/1965 | Wight et al. |
| 3,201,356 A | 8/1965 | Kress et al. |
| 3,347,945 A | 10/1967 | Slaugh |
| 3,390,101 A | 6/1968 | Csicsery |
| 3,412,165 A | 11/1968 | Slaugh et al. |
| 3,536,771 A | 10/1970 | Graff |
| 3,760,017 A | 9/1973 | Arkell et al. |
| 3,760,018 A | 9/1973 | Suggitt et al. |
| 3,760,019 A | 9/1973 | Crone, Jr. et al. |
| 3,784,617 A | 1/1974 | Suggitt et al. |
| 3,784,618 A | 1/1974 | Suggitt et al. |
| 3,786,106 A | 1/1974 | Zuech et al. |
| 3,839,477 A | 10/1974 | Suggitt et al. |
| 3,864,421 A | 2/1975 | Suggitt |
| 3,957,687 A | 5/1976 | Arkell et al. |
| 3,962,362 A | 6/1976 | Suggitt |
| 4,021,490 A | 5/1977 | Hudson |
| 4,094,918 A | 6/1978 | Murtha et al. |
| 4,122,125 A | 10/1978 | Murtha et al. |
| 4,152,362 A | 5/1979 | Murtha |
| 4,177,165 A | 12/1979 | Murtha et al. |
| 4,206,082 A | 6/1980 | Murtha et al. |
| 4,219,687 A | 8/1980 | Dolhyj et al. |
| 4,219,689 A | 8/1980 | Murtha |
| 4,268,699 A | 5/1981 | Murtha et al. |
| 4,329,531 A | 5/1982 | Murtha et al. |
| 4,380,683 A | 4/1983 | Dolhyj et al. |
| 4,439,409 A | 3/1984 | Puppe et al. |
| 4,447,554 A | 5/1984 | Murtha et al. |
| 4,463,207 A | 7/1984 | Johnson |
| 4,826,667 A | 5/1989 | Zones et al. |
| 4,954,325 A | 9/1990 | Rubin et al. |
| 4,962,250 A | 10/1990 | Dessau et al. |
| 5,037,538 A | 8/1991 | Chin et al. |
| 5,053,571 A | 10/1991 | Makkee |

(Continued)

FOREIGN PATENT DOCUMENTS

| | | |
|---|---|---|
| EP | 0 293 032 | 11/1988 |
| EP | 0 338 734 | 10/1989 |

(Continued)

OTHER PUBLICATIONS

Ruan et al., "Structure Elucidation of the Highly Active Titanosilicate Catalyst Ti-YNU-1", Angewandte Chemie International Edition, 2005, vol. 44, pp. 6719-6723.

W. Fan et al., "Synthesis and Catalytic Properties of a New Titanosilicate Molecular Sieve with the Structure Analogous to MWW-type Lamellar Precursor", Journal of Catalyst, 2006, vol. 243, pp. 183-191.

S. Kim et al., "Structural Evolution of B-MCM-36 and B-ITQ-2 from B-MCM-22", Bull. Korean Chem. Society, 2006, vol. 27, No. 10, pp. 1693-1696.

S. Lawton et al., "Zeolite MCM-49: A Three-Dimensional MCM-22 Analogue Synthesized by in Situ Crystallization", Journal of Physical Chemistry, 1996, vol. 100, pp. 3788-3798.

(Continued)

*Primary Examiner* — Sikarl Witherspoon
(74) *Attorney, Agent, or Firm* — Jamie L. Sullivan; Siwen Chen (57) ABSTRACT

In a process for producing cyclohexylbenzene, benzene and hydrogen are fed to at least one reaction zone comprising a catalyst system which comprises a molecular sieve and at least one hydrogenation metal. The MCM-22 family molecular sieve having an X-ray diffraction pattern including d-spacing maxima at 12.4±0.25, 6.9±0.15, 3.57±0.07 and 3.42±0.07 Angstrom, and the hydrogenation metal is selected from the group consisting of palladium, ruthenium, nickel, zinc, tin, cobalt, and combinations of any two or more thereof. Hydroalkylation conditions of temperature and pressure are selected to produce a hydroalkylation conversion in a range of from about 15% to about 75% The benzene and hydrogen are then contacted in the at least one reaction zone under said selected hydroalkylation condition to produce an effluent containing cyclohexylbenzene.

20 Claims, 3 Drawing Sheets

(56) References Cited

U.S. PATENT DOCUMENTS

| | | | |
|---|---|---|---|
| 5,108,969 | A | 4/1992 | Del Rossi et al. |
| 5,118,896 | A | 6/1992 | Steigelmann et al. |
| 5,146,024 | A | 9/1992 | Reed |
| 5,236,575 | A | 8/1993 | Bennett et al. |
| 5,250,277 | A | 10/1993 | Kresge et al. |
| 5,292,976 | A | 3/1994 | Dessau et al. |
| 5,326,697 | A | 7/1994 | Magers |
| 5,334,795 | A | 8/1994 | Chu et al. |
| 5,362,697 | A | 11/1994 | Fung et al. |
| 5,384,296 | A | 1/1995 | Tsao |
| 5,488,194 | A | 1/1996 | Beck et al. |
| 5,554,274 | A | 9/1996 | Degnan et al. |
| 5,557,024 | A | 9/1996 | Cheng et al. |
| 5,705,729 | A | 1/1998 | Huang |
| 6,037,513 | A | 3/2000 | Chang et al. |
| 6,077,498 | A | 6/2000 | Diaz Cabanas et al. |
| 6,133,470 | A | 10/2000 | Beck et al. |
| 6,489,529 | B1 | 12/2002 | Cheng et al. |
| 6,504,070 | B2 | 1/2003 | Matsumoto et al. |
| 6,506,953 | B1 | 1/2003 | Cheng et al. |
| 6,730,625 | B1 | 5/2004 | Chang et al. |
| 6,781,025 | B2 | 8/2004 | Dandekar et al. |
| 6,936,744 | B1 | 8/2005 | Cheng et al. |
| 7,488,861 | B2 | 2/2009 | Boyer et al. |
| 7,579,511 | B1 | 8/2009 | Dakka et al. |
| 7,842,277 | B2 | 11/2010 | Roth et al. |
| 7,910,778 | B2 | 3/2011 | Chen et al. |
| 7,959,899 | B2 | 6/2011 | Roth et al. |
| 2003/0083527 | A1 | 5/2003 | Kuhnle et al. |
| 2004/0092757 | A1 | 5/2004 | Oguchi et al. |
| 2005/0158238 | A1 | 7/2005 | Tatsumi et al. |
| 2008/0027256 | A1 | 1/2008 | Roth et al. |
| 2008/0027259 | A1 | 1/2008 | Roth et al. |
| 2008/0045768 | A1 | 2/2008 | Roth et al. |
| 2011/0037022 | A1 | 2/2011 | Dakka et al. |

FOREIGN PATENT DOCUMENTS

| | | |
|---|---|---|
| EP | 0 387 080 | 9/1990 |
| JP | 2005-342644 | 12/2005 |
| WO | 95/31421 | 11/1995 |
| WO | 97/17290 | 5/1997 |
| WO | 01/53236 | 7/2001 |
| WO | 01/74767 | 10/2001 |
| WO | 2005/118476 | 12/2005 |
| WO | 2009/021604 | 2/2009 |
| WO | 2009/038900 | 3/2009 |
| WO | 2009/131769 | 10/2009 |
| WO | 2011/001244 | 1/2011 |

OTHER PUBLICATIONS

S. Maheshwari et al., "*Layer Structure Preservation During Swelling, Pillaring, and Exfoliation of a Zeolite Precursor*", Journal of American Chemical Soc., 2008, vol. 130, pp. 1507-1516.

L. Slaugh et al., "*Hydrodimerization of Benzene to Phenylcyclohexane over Supported Transition Metal Catalysts*", Journal of Catalysis, 1969, vol. 13, pp. 385-396.

P. Wu et al., "*Methodology for Synthesizing Crystalline Metallosilicates with Expanded Pore Windows Through Molecular Alkoxysilylation of Zeolitic Lamellar Precursors*", Journal of American Chemical Soc., 2008, vol. 130, pp. 8178-8187.

L. Zhicheng et al., "*Static Synthesis of High-Quality MCM-22 Zeolite with High $SiO_2/Al_2O_3$ Ratio*", Chinese Science Bull., 2004, vol. 49, No. 6, pp. 556-561.

Borodina et al., "*Hydroalkylation of Benzene and Ethylbenzene Over Metal Containing Zeolite Catalysts*", Microporous and Mesoporous Materials, 2007, vol. 105, pp. 181-188.

PROCESS FOR PRODUCING CYCLOHEXYLBENZENE

CROSS REFERENCE TO RELATED APPLICATIONS

This application is a National Stage Application of International Application No. PCT/US2009/065692 filed Nov. 24, 2009, which claims the benefit of prior U.S. provisional application Ser. No. 61/155,733 filed Feb. 26, 2009, both of which are hereby incorporated by reference in their entirety.

FIELD

The present invention relates to a process for producing cyclohexylbenzene under selected hydroalkylation conditions, and optionally for converting the resultant cyclohexylbenzene into phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that uses higher alkenes instead of propylene as feed and coproduces higher ketones, rather than acetone, may be an attractive alternative route to the production of phenols.

For example, oxidation of cyclohexylbenzene (analogous to cumene oxidation) could offer an alternative route for phenol production without the problem of acetone co-production. This alternative route co-produces cyclohexanone, which has a growing market and is used as an industrial solvent, as an activator in oxidation reactions, and in the production of adipic acid, cyclohexanone resins, cyclohexanone oxime, caprolactam and nylon 6. However, this alternative route requires the development of a commercially-viable process for producing the cyclohexylbenzene precursor.

It has been known for many years that cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffer from the problems that the selectivity to cyclohexylbenzene is low, particularly at economically viable benzene conversion rates, and that large quantities of unwanted by-products, particularly cyclohexane and methylcyclopentane, are produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of from about 50 to 350° C., a pressure of from about 100 to 7000 kPa, a benzene to hydrogen molar ratio of from about 0.01 to 100 and a WHSV of from about 0.01 to 100. The '513 patent discloses that the resultant cyclohexylbenzene can then be oxidized to the corresponding hydroperoxide and the peroxide decomposed to the desired phenol and cyclohexanone.

According to the present invention, it has now been found that in the hydroalkylation of benzene over a bifunctional catalyst comprising an MCM-22 family zeolite and a hydrogenation metal, the selectivity to cyclohexylbenzene, and it dialkylated counterpart, dicyclohexylbenzene, is highly dependent on the conversion rate of benzene feedstock. The selectivity of cyclohexylbenzene is the mathematical quotient of the hydroalkylation conversion rate (i.e., benzene conversion rate when benzene is the limiting reactant) divided by the cyclohexylbenzene yield. In particular, it is found that the selectivity of cyclohexylbenzene is optimized when the hydroalkylation conversion rate is especially in the range of from about 15% to about 75%. In this range of hydroalkylation conversion, the cyclohexylbenzene selectivity is optimized and ranges of from about 45% to about 85%, while the selectivity to dicyclohexylbenzene ranges of from about 5% to about 40%.

SUMMARY

In one embodiment, the present invention is a process for producing cyclohexylbenzene, the process comprising:

(a) feeding benzene and hydrogen to at least one reaction zone comprising a catalyst system, said catalyst system comprising a MCM-22 family molecular sieve and at least one hydrogenation metal, said MCM-22 family molecular sieve having an X-ray diffraction pattern including d-spacing maxima at 12.4±0.25, 6.9±0.15, 3.57±0.07 and 3.42±0.07 Angstrom;

(b) selecting hydroalkylation conditions for said at least one reaction zone to produce a hydroalkylation conversion in a range of from about 15% to about 75%, said hydroalkylation conditions include a hydroalkylation temperature within the range from about 125° C. to about 175° C. and a hydroalkylation pressure within the range from about 125 psig (862 kPag) to about 175 psig (1227 kPag); and (c) contacting said benzene and said hydrogen in said reaction zone under said selected hydroalkylation conditions in said reaction zone wherein the ratio of the total number of moles of hydrogen fed to the at least one reaction zone to the total number of moles of benzene fed to the at least one reaction zone is from about 0.35 to about 1.35. Preferably, said hydroalkylation conversion is in a range of from about 20% to about 70%; more preferably, said hydroalkylation conversion is in a range of from about 25% to about 65%; and most preferably, hydroalkylation conversion is in a range of from about 30% to about 60%.

Advantageously, in the prevent hydroalkylation process the selectivity to cyclohexylbenzene is in a range of from about 45% to about 85%.

Conveniently, said selected hydroalkylation conditions of temperature is selected in the range of from about 135° C. to about 165° C.

Conveniently, said selected hydroalkylation conditions of pressure is selected in the range of from about 125 psig (862 kPag) to about 175 psig (1227 kPag).

Conveniently, said selected hydroalkylation conditions include a weight hourly space velocity of benzene is in the range of from about 0.26 to about 1.35 $hr^{-1}$.

Conveniently, the MCM-22 family molecular sieve is selected from the group consisting of MCM-22, PSH-3, SSZ-25, ERB-1, ITQ-1, ITQ-2, MCM-36, MCM-49, MCM-56, UZM-8 and mixtures of any two or more thereof, and preferably MCM-22, MCM-49, MCM-56, and combinations of two or more thereof.

Conveniently, said at least one hydrogenation metal is selected from palladium, ruthenium, nickel, zinc, tin, and cobalt.

Preferably, said molecular sieve is MCM-49 and said at least one hydrogenation metal is palladium.

In another embodiment, the process further comprises the step of selecting a ratio of the total number of moles of hydrogen fed to the at least one reaction zone to the total number of moles of benzene fed to the at least one reaction zone in a range of from about 0.15 to about 15, to produce said hydroalkylation conversion.

In still another embodiment, the invention resides in a method for coproducing phenol and cyclohexanone, the method comprising producing cyclohexylbenzene by any one of the processes described herein, oxidizing the cyclohexylbenzene to produce cyclohexylbenzene hydroperoxide and cleaving the cyclohexylbenzene hydroperoxide to produce phenol and cyclohexanone.

DETAILED DESCRIPTION

Described herein is a process for the hydroalkylation of benzene to produce cyclohexylbenzene under selected hydroalkylation conditions. The cyclohexylbenzene so produced may be converted to cyclohexanone and phenol in a two step process. Insofar as the hydroalkylation step produces dicyclohexylbenzene in addition to the desired cyclohexylbenzene product, the process can include the further step of transalkylating the dicyclohexylbenzene with additional benzene to produce additional cyclohexylbenzene product. As used herein, the "cyclohexylbenzene" means monocyclohexylbenzene.

Hydroalkylation Process

The first step in one embodiment of the present hydroalkylation process of this invention comprises feeding benzene and hydrogen to at least one reaction zone comprising a catalyst system. The catalyst system (described in more detail below) comprises a MCM-22 family molecular sieve and at least one hydrogenation metal.

In the second step, hydroalkylation conditions are selected for said at least one reaction zone to produce a benzene conversion in a range of from about 15% to less than or equal to about 75%, said hydroalkylation conditions comprising at least a temperature and a pressure of said at least one reaction zone.

In the third step, benzene and hydrogen are contacted under said selected hydroalkylation conditions in said reaction zone to produce an effluent containing cyclohexylbenzene.

Preferably, said hydroalkylation conversion is in a range of from about 20% to about 70%, more preferably, said hydroalkylation conversion is in a range of from about 25% to about 65%; and most preferably, hydroalkylation conversion is in a range of from about 30% to about 60%.

It has been discovered that the selected hydroalkylation conditions to produce said hydroalkylation conversion in said at least one reaction zone advantageously include a temperature selected in the range of from about 100° C. to about 400° C.; preferably, a temperature selected in the range of from about 125° C. to about 375° C.; more preferably, a temperature selected in the range of from about 150° C. to about 325° C.; and most preferably, a temperature selected in the range of from about 125° C. to about 175° C. In another embodiment, said hydroalkylation temperature is selected in the range of from about 135 to about 155° C. or about 145 to about 155° C.

It has also been discovered that the selected hydroalkylation conditions in said at least one reaction zone advantageously include a pressure selected in the range of from about 125 psig (862 kPag) to about 175 psig (1227 kPag); preferably, a pressure selected in the range of from about 135 psig (931 kPag) to about 165 psig (1138 kPag); more preferably, a pressure selected in the range of from about 145 psig (1000 kPag) to about 155 psig (1069 kPag).

In one or more embodiments of the present process of this invention, said selected hydroalkylation conditions include a weight hourly space velocity (WHSV) of hydrogen and benzene fed to said at least one reaction zone is selected in the range of from about 0.1 $hr^{-1}$ to about 100 $hr^{-1}$; preferably, selected in the range of from about 0.2 $hr^{-1}$ to about 50 $hr^{-1}$; more preferably, selected in the range of from about 0.3 $hr^{-1}$ to about 25 $hr^{-1}$; and most preferably, a selected WHSV of about 0.5 $hr^{-1}$. In another embodiment, said weight hourly space velocity is in the range of from about 0.35 to about 0.95 $hr^{-1}$, about 0.45 to about 0.75 $hr^{-1}$, or about 0.45 to about 0.55 $hr^{-1}$.

It has also been discovered that the present process further comprises the step of advantageously selecting a ratio of the total number of moles of hydrogen fed to the at least one reaction zone to the total number of moles of benzene fed to the at least one reaction zone (hydrogen to benzene molar ratio) in a range of from about 0.15 to about 15, to produce said hydroalkylation conversion in a range of from about 15% to about 75%, said hydroalkylation conditions.

Preferably, the hydrogen to benzene molar ratio is selected in the range of from about 0.20 to about 10; more preferably, the hydrogen to benzene molar ratio is selected in the range of from about 0.25 to about 5; and most preferably, the hydrogen to benzene molar ratio is selected in a range of from about 0.30 to about 1.40. In another embodiment, said hydrogen to benzene molar ratio is selected in the range of from about 0.26 $hr^{-1}$ to about 1.35 $hr^{-1}$, about 0.35 to about 1.35, about 0.45 to about 0.95, about 0.55 to about 0.75, and about 0.55 to about 0.65.

Advantageously, it has been discovered that the selectivity to cyclohexylbenzene is in a range of from about 45% to about 85%, when the hydroalkylation conversion is in the range of from about 15% to about 75%. Preferably, the selectivity to cyclohexylbenzene is in a range of from about 45% to about 85%; more preferably, the selectivity to cyclohexylbenzene is in a range of from about 50% to about 80%; and most preferably, the selectivity to cyclohexylbenzene is in a range of from about 55% to about 75%.

Advantageously, it has been discovered that the selectivity to dicyclohexylbenzene is in the range of from about 5% to about 40%, when the hydroalkylation conversion is in the range of from about 15% to about 75%. Preferably, the selectivity to dicyclohexylbenzene is in the range of from about 10% to about 35%; more preferably, the selectivity to dicyclohexylbenzene is in the range of from about 15% to about 30%; most preferably, the selectivity to dicyclohexylbenzene is about 20%.

In the present process, described above, benzene undergoes the following reaction to produce cyclohexylbenzene:

Competing reactions include the complete saturation of the benzene to produce cyclohexane, dialkylation to produce dicyclohexylbenzene and reorganization/alkylation reactions to produce impurities, such as methylcyclopentylbenzene (MCPB). Although dicyclohexylbenzene can be transalkylated to produce additional cyclohexylbenzene product, conversion to cyclohexane represents loss of valuable feed, whereas impurities such as MCPB are particularly undesirable since the boiling point of MCPB is very close to that of cyclohexylbenzene so that it is very difficult to separate MCPB from cyclohexylbenzene. It is therefore important to minimize the production of MCPB impurity in the hydroalkylation reaction.

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Preferably, the total feed to the hydroalkylation step contains less than 1000 ppm, such as less than 500 ppm, for example less than 100 ppm, water. Preferably, the total feed typically contains less than 100 ppm, such as less than 30 ppm, for example less than 3 ppm, sulfur. Preferably, the total feed contains less than 10 ppm, such as less than 1 ppm, for example less than 0.1 ppm, nitrogen. In a particularly preferred embodiment at least two, and preferably all three of the above mentioned preferred levels for water, sulfur and nitrogen are achieved.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages.

The reaction zone(s) are preferably located in a single reactor vessel, but may include another reaction zone having an alkylation or transalkylation catalyst bed, located in separate vessel which may be a by-passable and which may operate as a reactive guard bed (as described below).

The catalyst system used in the reactive guard bed may be different from the catalyst system used in the reaction zone. The catalyst system used in the reactive guard bed may have multiple catalyst compositions. At least one reaction zone, and normally each reaction zone, is maintained under conditions effective to cause hydroalkylation of benzene in the presence of the hydroalkylation catalyst system and/or transalkylation of dicyclohexylbenzene in the presence of a transalkylation catalyst system.

In addition to, and upstream of, the reaction zones, a by-passable reactive or unreactive guard bed may normally be located in a reactor zone separate from the hydroalkylation reactor. Such guard bed may also be loaded with a hydroalkylation or transalkylation catalyst systems, which may be the same or different from the catalyst system used in the other reaction zone(s). Such guard bed is maintained from under ambient conditions, or at suitable hydroalkylation or transalkylation conditions. At least a portion of the benzene is passed through the unreactive or reactive guard bed prior to entry into a reaction zone. These guard beds not only serve to affect the desired hydroalkylation reaction, but is also used to remove at least a portion of any reactive impurities in the benzene feed, such as nitrogen compounds, which could otherwise poison the remainder of the alkylation or transalkylation catalyst systems. The catalyst system in the reactive or unreactive guard bed is therefore subject to more frequent regeneration and/or replacement than the remainder of the hydroalkylation or transalkylation catalyst systems, and hence the guard bed is typically provided with a by-pass circuit so that the hydroalkylation feeds may be fed directly to the series-connected reaction zones in the hydroalkylation reactor while the guard bed is out of service. The reactive or unreactive guard bed may be operated in co-current upflow or downflow operation.

While not being bound by any particular theory, it is believed that by controlling the hydroalkylation conditions of temperature, pressure, the hydrogen to benzene molar ratio and the weight hourly space velocity of benzene and hydrogen, to produce a hydroalkylation conversion in the range of from about 15% to about 75%, the cyclohexylbenzene selectivity is optimized at an acceptable dicyclohexylbenzene selectivity. As can be seen from the ensuing Example, stable performance was obtained in hydroalkylation of benzene to cyclohexylbenzene and dicyclohexylbenzene when hydroalkylation conversion was between 15-75% over an MCM-49/Pd hydroalkylation catalyst. No deactivation in catalyst activity or selectivity was obtained in over two months of operations when conversion is in the preferred range. The stable performance was highly unexpected because the main products from the reaction are cyclohexylbenzene and dicyclohexylbenzene, both of which have boiling points well in excess of 200° C.

Hydroalkylation Catalyst System

The catalyst employed in the hydroalkylation reaction is a bifunctional catalyst comprising a molecular sieve of the MCM-22 family and a hydrogenation metal. The term "MCM-22 family molecular sieve" (or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as the incident radiation and a diffractometer equipped with a scintillation counter and associated computer as the collection system. Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), their isotypes, and mixtures of any two or more thereof. Preferably, the molecular sieve is selected from the group consisting of MCM-22, MCM-49 and MCM-56, their isotypes, and mixtures or combinations of any two or more thereof.

Any known hydrogenation metal can be employed in the present hydroalkylation catalyst although suitable metals include palladium, ruthenium, nickel, zinc, tin, and cobalt, and combinations thereof, with palladium being particularly advantageous. Generally, the amount of hydrogenation metal present in the catalyst is between about 0.05% and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, incipient wetness, impregnation, ion exchange or by extrusion techniques. However, in a more preferred embodiment, at least 50 wt %, for example at least 75 wt % and generally substantially all of the hydrogenation metal is supported on an inorganic oxide separate from but composited with the molecular sieve. In particular, it is believed that by supporting the hydrogenation metal on the inorganic oxide, the activity of the catalyst and its selectivity to cyclohexylbenzene is increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina and/or titania and/or zirconia. As used herein, the numbering scheme for the Periodic Table Groups is as disclosed in Chemical and Engineering News, 63(5), 27 (1985). When the catalyst system comprises a composite of the molecular sieve and the inorganic oxide that is different from the molecular sieve, these two components are conveniently present in a weight ratio in the range 90:10 to 10:90, such as 80:20 to 20:80, for example 70:30 to 30:70 or 60:40 to 40:60.

In the above-mentioned preferred embodiment, the hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Transalkylation

Although the hydroalkylation step is highly selective towards cyclohexylbenzene, the effluent from the hydroalkylation reaction will normally contain some dialkylated products, as well as unreacted aromatic feed and the desired monoalkylated species (e.g. cyclohexylbenzene). The unreacted aromatic feed is normally recovered by distillation and recycled to the alkylation reactor. The bottoms from the benzene distillation are further distilled to separate the cyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species (e.g. cyclohexylbenzene).

Transalkylation with additional benzene is typically affected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C. and/or a pressure of about 800 to about 3500 kPa and/or a weight hourly space velocity of about 1 to about 10 hr$^{-1}$ on total feed and/or a benzene/dicyclohexylbenzene weight ratio about of 1:1 to about 5:1.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaricimide), N-hydroxy-5-norbornene-2,3-dicarboximide, exo-N-hydroxy-7-oxabicyclo[2,2,1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-trihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, such as between 0.001 to 5 wt %, of the cyclohexylbenzene.

Suitable conditions for the oxidation step include a temperature between about 70° C. and about 200° C., such as about 90° C. to about 130° C., and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase. This is conveniently carried out at a temperature of about 20° C. to about 150° C., such as about 40° C. to about 120° C. and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes smectite clay, such as acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species.

The following Example is given for illustrative purposes and does not limit the scope of the invention.

Example 1

A series of experiments was conducted in which benzene and hydrogen was contacted with a catalyst system prepared by co-pelletizing 2 g of a Pd/Al$_2$O$_3$ catalyst with 6 g of a MCM-49/Al$_2$O$_3$ catalyst. The Pd concentration of the Pd/Al$_2$O$_3$ catalyst was 0.3 wt %. The concentration of MCM-49 of the MCM-49 Al$_2$O$_3$ catalyst was 80%.

Figure 1:
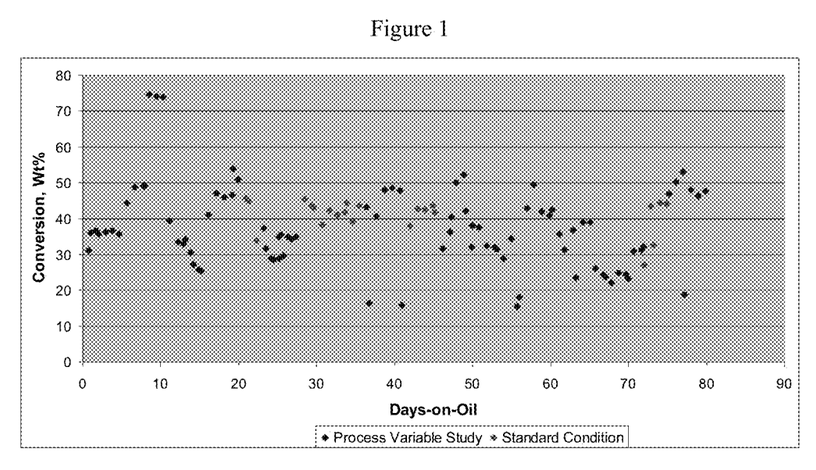
FIG. 1 is a graph of benzene conversion as a function of days-on-oil for the hydroalkylation process of Example 1.
Figure 2:
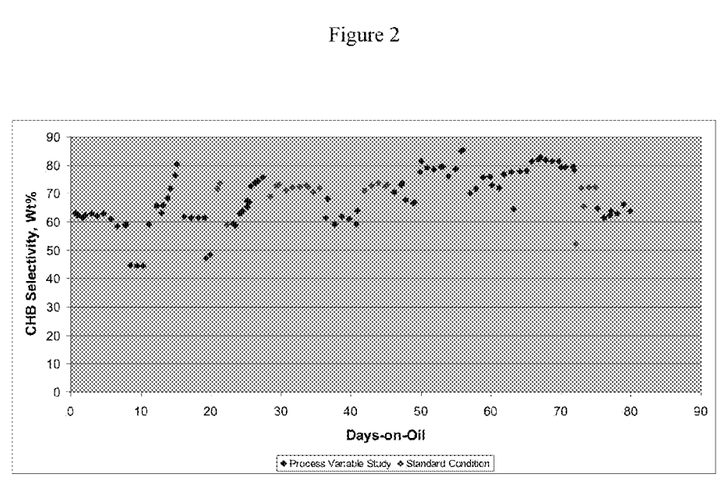
FIG. 2 is a graph of cyclohexylbenzene selectivity as a function of days-on-oil for the hydroalkylation process of Example 1.
Figure 3:
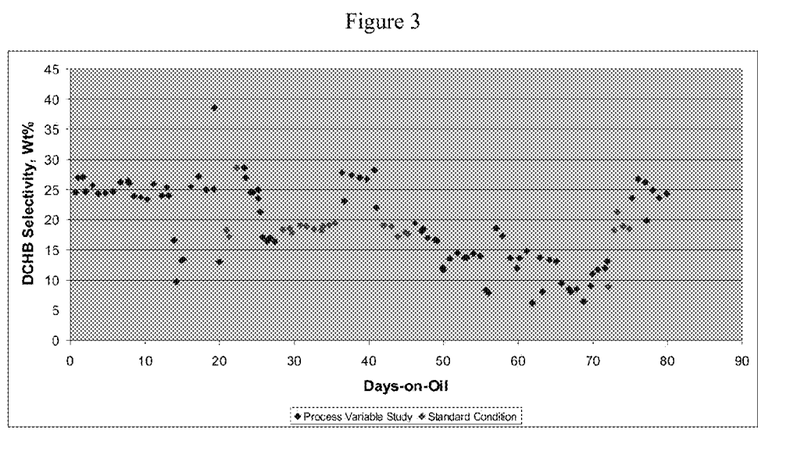
FIG. 3 is a graph of dicyclohexylbenzene selectivity as a function of days-on-oil for the hydroalkylation process of Example 1.

In this study, the hydroalkylation conversion was varied between 15% and 75%. The reactor temperature was varied between 125° C. and 175° C. The pressure was varied between 963 kPa-a (125 psig) and 1308 kPa-a (175 psig). The molar ratio of hydrogen to benzene was varied between 0.35 and 1.35. The material balances were completed at the "standard" conditions of 150° C., 1135 kPa-a (164.7 psig), 0.64 hydrogen/benzene molar feed ratio, and 0.5 hr$^{-1}$ weight hourly space velocity (WHSV) periodically in order to determine the stability of the hydroalkylation process. The benzene feed used in the study was pretreated with a series of guard beds comprised of 13X, 4A, clay, Selexsorb CD, and MCM-49/Al$_2$O$_3$ before the feed was introduced into the reactor. The results are shown in FIGS. 1 to 3. The materials.

As can be seen from FIGS. 1-3, conversion ranged between 15-75% as a result of the process changes. The selectivity to cyclohexylbenzene ranged from 45 to 85% while the selectivity to dicyclohexylbenzene ranged from 5 to 40%. The average conversion of the run is 38% while the average selectivity to cyclohexylbenzene and dicyclohexylbenzene are 68% and 19%, respectively.

On days 21-22, 28-35, 42-45, and 72-75, the unit was operated at 150° C., 1135 kPa-a (150 psig), and a hydrogen/benzene molar feed ratio of 0.64 and 0.5 hr$^{-1}$ WHSV. At the "standard" condition, the average conversion is 42% while selectivity to cyclohexylbenzene and dicyclohexylbenzene is 72% and 18%, respectively. The stable conversion and high selectivity to cyclohexylbenzene and dicyclohexylbenzene was highly unexpected because the two main products of the reaction are both very heavy, with boiling points in excess of 200° C. Another reason that the stable performance was unexpected was that the conversion had been as high as 75%, yet the catalyst performance continued to be excellent.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing cyclohexylbenzene, the process comprising:
   (a) feeding benzene and hydrogen to at least one reaction zone comprising a catalyst system, said catalyst system comprising a MCM-22 family molecular sieve and at least one hydrogenation metal, said MCM-22 family molecular sieve having an X-ray diffraction pattern including d-spacing maxima at 12.4±0.25, 6.9±0.15, 3.57±0.07 and 3.42±0.07 Angstrom;
   (b) adjusting hydroalkylation conditions for said at least one reaction zone to produce a hydroalkylation conversion in a range of from about 15% to about 75% wherein said hydroalkylation conditions include a hydroalkylation temperature within the range of from about 125° C. to about 175° C. and a hydroalkylation pressure within the range of from about 125 psig (862 kPag) to about 175 psig (1227 kPag), such that the selectivity to cyclohexylbenzene is in a range from about 45% to about 85%; and
   (c) contacting said benzene and said hydrogen in said reaction zone wherein the ratio of the total number of moles of hydrogen fed to the at least one reaction zone to the total number of moles of benzene fed to the at least one reaction zone is from about 0.45 to about 0.95.

2. The process of claim 1, wherein said hydroalkylation conditions of temperature is in the range of from about 135° C. to about 165° C.

3. The process of claim 1, wherein said hydroalkylation conditions of pressure is in the range of from about 931 kPag to about 1138 kPa-a.

4. The process of claim 1, wherein said hydroalkylation conditions include a weight hourly space velocity in the range of from about 0.26 hr$^{-1}$ to less than about 1.35 hr$^{-1}$.

5. The process of claim 1, wherein said MCM-22 family molecular sieve is selected from the group consisting of MCM-22, PSH-3, SSZ-25, ERB-1, ITQ-1, ITQ-2, MCM-36, MCM-49, MCM-56, UZM-8 and combinations of any two or more thereof.

6. The process of claim 1, wherein said at least one hydrogenation metal is selected from the group consisting of palladium, ruthenium, nickel, zinc, tin, cobalt, and combinations of any two or more thereof.

7. The process of claim 1, wherein said molecular sieve is MCM-49 and said at least one hydrogenation metal is palladium.

8. The process of claim 1, wherein said at least one hydrogenation metal is present in an amount from about 0.05% to about 10% by weight of the catalyst system.

9. The process of claim 1, wherein said benzene is passed through a reactive guard bed to remove at least a portion of reactive impurities, said reactive impurities comprising nitrogen compounds.

10. The process of claim 1, wherein said portion of the hydrogenation metal is supported on an inorganic oxide different from the molecular sieve.

11. The process of claim 10, wherein said inorganic oxide comprises an oxide of at least one element of Groups 2, 4, 13 and 14 of the Periodic Table of Elements.

12. The process of claim 10, wherein said inorganic oxide is selected from the group consisting of alumina, titania, zirconia and combinations of two or more thereof.

13. The process of claim 1, wherein said effluent further comprises dicyclohexylbenzene and at least part of the dicyclohexylbenzene is contacted with additional benzene under transalkylation conditions to produce addition cyclohexylbenzene.

14. The process of claim 1, wherein the benzene conversion is in the range of from about 30% to about 60%.

15. The process of claim 1, further comprising the step of selecting a ratio of the total number of moles of hydrogen fed to the at least one reaction zone to the total number of moles of benzene fed to the at least one reaction zone in a range of from about 0.55 to about 0.75, to produce said hydroalkylation conversion.

16. The process of claim 1, wherein said hydroalkylation conditions of temperature is in the range of from about 145° C. to about 155° C., said hydroalkylation conditions of pressure is in the range of from about 931 kPag to about 1138 kPag.

17. The process of claim 1, wherein said MCM-22 family molecular sieve is selected from the group consisting of MCM-22, PSH-3, SSZ-25, ERB-1, ITQ-1, ITQ-2, MCM-36, MCM-49, MCM-56, UZM-8 and combinations of any two or more thereof, and said at least one hydrogenation metal is selected from the group consisting of palladium, ruthenium, nickel, zinc, tin, cobalt, and combinations of any two or more thereof.

18. The process of claim 1, wherein said at least one reaction zone is a fixed bed reactor.

19. A method for coproducing phenol and cyclohexanone, the method comprising the steps of producing cyclohexylbenzene by the process of claim 1, oxidizing the cyclohexylbenzene to produce cyclohexylbenzene hydroperoxide and cleaving the cyclohexylbenzene hydroperoxide to produce phenol and cyclohexanone.

20. A process of claim 1, wherein the step (b) comprises adjusting hydroalkylation conditions for said at least one reaction zone to produce a hydroalkylation conversion in a range of from about 20% to about 30%.

* * * * *